United States Patent [19]

Daniel et al.

[11] Patent Number: 5,294,540
[45] Date of Patent: Mar. 15, 1994

[54] ETHANOL ANALYTICAL ELEMENT

[75] Inventors: Daniel S. Daniel, Rochester; Karen L. Warren, Rush; James R. Schaeffer, Penfield, all of N.Y.

[73] Assignee: Eastman Kodak Company, Rochester, N.Y.

[21] Appl. No.: 829,663

[22] Filed: Feb. 3, 1992

Related U.S. Application Data

[63] Continuation-in-part of Ser. No. 556,640, Jul. 5, 1990, abandoned.

[51] Int. Cl.$^5$ .................. C12Q 1/26; G01N 33/00
[52] U.S. Cl. ..................... 435/25; 435/805; 435/970; 436/132
[58] Field of Search ............ 435/25, 805, 970; 436/132

[56] References Cited

U.S. PATENT DOCUMENTS

| | | | |
|---|---|---|---|
| 3,992,158 | 11/1976 | Pryzbylowicz et al. | 422/57 |
| 4,168,205 | 7/1979 | Danninger et al. | 435/10 |
| 4,671,937 | 6/1987 | Katsuyama et al. | 422/56 |
| 4,892,816 | 1/1990 | Akiba et al. | 435/11 |

FOREIGN PATENT DOCUMENTS

256196A1  2/1986  German Democratic Rep.

*Primary Examiner*—Douglas W. Robinson
*Assistant Examiner*—Jon P. Weber
*Attorney, Agent, or Firm*—John R. Everett

[57] ABSTRACT

A multilayer analytical element for quantitatively assaying ethanol comprising a tetrazolium salt, alcohol dehydrogenase, NAD+, and an electron transfer agent characterized in that the layer comprising the electron transfer agent also includes a polymer having recurring negatively charged groups and the NAD+ is in a different layer is disclosed.

8 Claims, No Drawings

ETHANOL ANALYTICAL ELEMENT

CROSS REFERENCE TO RELATED APPLICATIONS

This is a continuation-in-part application of our earlier filed application Ser. No. 556,640, filed on Jul. 5, 1990 now abandoned.

FIELD OF THE INVENTION

This invention relates to clinical chemistry, and in particular to an element for quantitatively assaying ethanol.

BACKGROUND OF THE INVENTION

Methods for qualitative and quantitative determination of ethanol in aqueous body fluids, particularly human body fluids, are used in medicine and in law enforcement.

In medicine, determination of ethanol in blood is significant in diagnosing liver malfunction and alcoholism. In law enforcement, such assays are used to determine whether an automobile operator is or is not driving under the influence of alcohol.

East German Patent Publication DD 256,196 A1 discloses a test strip for determining ethanol content in biological fluids. The test strip is based on the following series of chemical reactions:

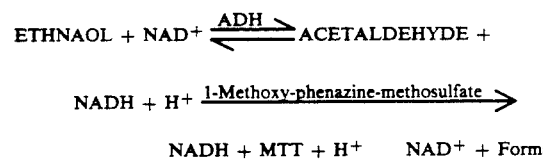

$$NADH + MTT + H^+ \rightarrow NAD^+ + Formazan$$

wherein MTT is [3-(4,5-dimethylthiazolyl-2) 2,5-diphenyltetrazolium].

The test strip contains:
(1) a compound which is suitable for electron transfer such as 1-methoxy-phenazine methosulfate;
(2) a tetrazolium salt, in particular MTT[3 -(4,5-Dimethyl(thiazolyl-2)2,5-diphenyl tetrazolium], and/or INT[2-(4-iodophenyl)- 3-(4-nitrophenyl)-5-diphenyl tetrazolium];
(3) an alcohol dehydrogenase (ADH);
(4) a nicotinamide adenine dinucleotide (NAD+); and
(5) a buffer (pH 1-4), in particular a glycine/hydrochloric acid buffer and a buffer (pH of 7-9), in particular semicarbazide buffer.

The problem is that this element is not suitable for a quantitative assay of ethanol after a 1 to 2 weeks of storage at room temperature. Incorporation of the above chemicals into a dry multilayer element designed for quantitative assays of ethanol consistently underpredicts ethanol concentrations after only three weeks of keeping. In addition, the above prior art element is subject to interference from components of blood serum such as ascorbic acid.

SUMMARY OF THE INVENTION

The present invention overcomes the previously stated problems by providing a multilayer analytical element for quantitatively assaying ethanol comprising a tetrazolium salt, alcohol dehydrogenase, NAD+, and an electron transfer agent characterized in that the layer comprising the electron transfer agent also includes a polymer having recurring negatively charged groups and the alcohol dehydrogenase is in a different layer.

In a preferred embodiment, the forgoing element also includes ascorbate oxidase, which obviates ascorbic acid interference resulting from any ascorbic acid in test sample.

The element of this invention is useful for quantitative assays of ethanol after four weeks of storage. The element is free from interferences from blood serum components such as ascorbic acid, methanol, isopropanol, hemoglobulin, and bilirubin.

DETAILS OF THE INVENTION

A useful embodiment of the element of this invention have, but are not limited to, elements having the following configuration and content.

| | Ethanol Element | |
|---|---|---|
| | Coverage (g/m$^2$) | |
| | Useful Range | Actual Range |
| Reagent/Spreading Layer | | |
| Unitane | 25–75 | 54 |
| Cellulose Acetate | 1–20 | 8 |
| Surfactant Triton X100 | 0.1–2 | 0.7 |
| NAD+ | 2–8 | 6 |
| Estane | 1–5 | 3 |
| Tetrozolium Salt | 1–8 | 4 |
| Subbing Zone | | |
| N-Isopropyl Acrylamide | 0.1–1 | 0.4 |
| Reagent Layer Zone 1 (pH 7.6) | | |
| Unhardened Gelatin | 4–12 | 8 |
| TRIS Buffer | 2–8 | 4 |
| Alcohol Dehydrogenase | 5000–20000 | 10000 U/m$^2$ |
| Ascorbate Oxidase | 2000–12000 | 5000 U/m$^2$ |
| Surfactant TX-200 | 0.01–0.2 | 0.05 |
| Zonyl FSN or Surfactant TX-100 | 0.01–0.2 | 0.02 |
| Reagent Layer Zone 2 (pH 7.6) | | |
| Hardened Gelatin | 4–12 | 6 |
| TRIS Buffer | 1–8 | 2 |
| Phenothiazine Methosulfate | 0.01–0.2 | 0.1 |
| Surfactant Zonyl FSN or | 0.01–0.1 | 0.02 |
| Surfactant TX-100 | .01–0.1 | 0.02 |
| Surfactant Triton X-200 | 0.01–0.1 | 0.05 |

The above element is suitable for the analysis of ethanol in biological fluids in the range of 0–500 mg/dL with good precision and acceptable accuracy.

In general, any polymer or copolymer containing negatively-charged groups, for example, carboxylic acid or sulfonic acid groups, would be useful in the practice of this invention. Useful acid groups include acrylic acid, methacrylic acid, maleic acid, mesaconic acid, ethane suldonic acid.

Preferred polymers are the following:
Poly(methyl acrylate-co-2-sulfo-1,1-dimethylethyl acrylamide-co-2-acetoacetoxyethyl methacrylate);
Poly(2-hydroxyethyl methacrylate-co-2-acrylamido-2-methylpropane sulfonic acid sodium salt-co-acetoacetoxyethyl methacrylate);
Poly(acrylamide-co-2-acrylamido-2-methylpropane sulfonic acid, sodium salt). The preferred polymer coverage is 0.6 g/m$^2$. A useful range is about 0.1 to 4 g/m$^2$):

Useful electron transfer agents have the general formula:

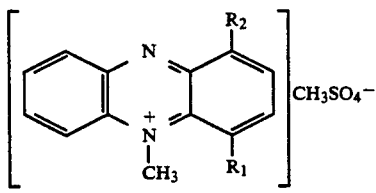

wherein $R_1$ may represent an alkyl group and $R_2$ an alkoxy group or a hydrogen atom preferred are 1-methoxy-5-methyl-phenazinium-methylsulfate (1-methoxyphenazine-methosulfate) and 5-ethyl-phenazinium-methylsulfate (phenazine-ethosulfate) in concentrations deemed catalytic based on the stoichiometery of the chemical reactions involved and the expected amount of ethanol in a particular sample.

The tetrazolium salt, the electron carrier component, include, for example; 3-(4,5-dimethylthiazolyl-2)-2,5-diphenyltetrazolium; 2-(4-iodophenyl)-3-(4-nitrophenyl)-5-phenyltetrazolium, 2,3,5-triphenyltetrazolium; nitro blue tetrazolium; blue tetrazolium tetranitro blue tetrazolium; thiocarbamyl nitro blue tetrazolium and the like. These salts are also used in stoichiometric amounts.

The enzyme alcohol dehydrogenase, ADH is used in stoichiometric amounts.

Nicotinamide adenine dinucleotide, $NAD^+$, acts as an oxidizing agent converting the ethanol to acetaldehyde generating NADH which reduces the tetrazolium salt into a colored formazane dye.

Examples of buffers suitable for use are glycine/hydrochloric acid buffers, semicarbazide/glycine buffers, tris buffers, phosphate buffers, phthalate buffers, citrate buffers, borate/succinate buffers and the like. Preferred buffers are semicarbazide/glycine buffers and glycine hydrochloric acid buffers in molar concentrations of 0.025 to 0.2.

DETAILED DESCRIPTION OF THE INVENTION

The element of this invention can be used to assay ethanol qualitatively and quantitatively in biological fluids in animals or humans, but preferably of humans. Such fluids include, but are not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like.

Elements of the invention can be configured in a variety of forms, including elongated tapes of any desired width, sheets, slides or chips.

The elements can be used in manual or automated assay techniques. In general, in using the elements, ethanol determination is made by taking the element from a supply roll, chip packet or other source and physically contacting it with a sample (for example, up to 200 ml) of the liquid to be tested so that the sample and reagents interact sequentially within the element become mixed. Such contact can be accomplished in any suitable manner, for example, by dipping or immersing the element into the sample or, preferably, by spotting the element by hand or machine with a drop of the sample with a suitable dispensing means.

After sample application, the element is incubated, for a period of up to 5 minutes, to facilitate color development. By incubation, we simply mean that the reagents are maintained in contact with each other for a period of up to 5 minutes before color measurements are made.

The dry analytical elements of this invention are multilayered. One of the layers is has a spreading function. In one embodiment the element includes a combined reagent/spreading layer along with an additional reagent layer having at least two distinct zones. All of the foregoing layers is coated on a support. The layers are generally in fluid contact with each other, meaning that fluids, reagents and reaction products (for example, color dyes) can pass or be transported between superposed regions of adjacent zones. In other words, when the element is contacted with an aqueous fluid, all reagents of the analytical composition of this invention mixed sequentially as stated hereinbefore and can readily move within the element as a composition. Each layer can be separate or two or more zones can be separate areas in a single layer of the element. Besides the references noted above, suitable element components are described also, for example, in U.S. Pat. No. 4,042,335 (issued Aug. 16, 1977 to Clément), U.S. Pat. No. 4,132,528 (issued Jan. 2, 1979 to Eikenberry et al), and U.S. Pat. No. 4,144,306 (issued Mar. 13, 1979 to Figueras).

Useful spreading layers can be prepared using fibrous materials, either mixed with a suitable binder material or woven into a fabric, as described in U.S. Pat. No. 4,292,272 (issued Sep. 29, 1981 to Kitajima et al), polymeric compositions or particulate materials, for example a blush polymer such as disclosed in U.S. Pat. No. 3,992,158, beads bound together with or without binding adhesives, as described in U.S. Pat. No. 4,258,001 (issued Mar. 24, 1981 to Pierce et al) and U.S. Pat. No. 4,430,436 (issued Feb. 7, 1984 to Koyama et al) and Japanese Patent Publication 57(1982)-101760. Particularly useful spreading layers comprise barium sulphate or titanium dioxide. Since the sample is generally applied directly to the spreading layer, it is desirable that the spreading layer be isotropically porous, meaning that the porosity is the same in each direction in the layer as caused by interconnected spaces or pores between particles, fibers or polymeric strands.

The elements of this invention can also contain one or more other addenda commonly put in the elements for various manufacturing or operational advantages. Such addenda include surfactants, bacteriostats, buffers, solvents, hardeners and other materials known in the art.

The layers can be coated on transparent supports such as polyethylene terephthalate. Other supports are well known in the art.

The following invention demonstrate the effectiveness of the present invention in maintaining the analytical capabilities of the ethanol analytical element over time.

Example 1: Keeping Comparison Using Elements With and Without Polymer Having recurring Negative Groups This example illustrates an ethanol assay comparing an element containing the negatively-charged polymer poly(methyl acrylate-co-2-sulfo- 1,1-dimethylethyl acrylamide-co-2-acetoacetoxyethyl methacrylate) with an element without the polymer after keeping the elements at 21° C. Except for the polymer both elements had the configuration and composition described, supra.

One version of each element was kept frozen [(−18° C. at 15% relative humidity (RH)] until tested. Then they were spotted with solutions containing human serum spiked with various concentrations of ethanol. After 5 minutes incubation at 37° C., the reflectance densities were measured at 540 nm. The ethanol concentrations obtained from these reflectance densities are the predicted concentrations for the various spiked alcohol levels.

A version of the element without the polymer was kept at room temperature (21° C. and 15% RH) for three weeks, and a version of the element containing the polymer were kept at room temperature for four weeks at 15% RH. These elements were then spotted with the same spiked solutions and assayed as above. The concentration values obtained were than compared to the predicted concentration values. Results are shown in Table I.

TABLE I

| Keeping Comparison with MaWnMt | | | | | |
|---|---|---|---|---|---|
| (Without Polymer) | | | (With Polymer) | | |
| Predicted Concentration Levels | Concentration After 3 Weeks Keeping (37° C.) (mg/dL) | Bias (mg/dL) | Predicted Concentration Levels (mg/dL) | Concentration After 4 Weeks Keeping (37° C.) (mg/dL) | Bias (mg/dL) |
| 1 | 2 | 3 | 4 | 5 | 6 |
| 0.0 | −4.66 | −4.66 | 0.0 | −7.71 | −7.71 |
| 97.9 | 81.93 | −15.97 | 96.07 | 94.33 | −1.74 |
| 107.0 | 86.56 | −20.44 | 106.91 | 104.87 | −2.04 |
| 119.56 | 90.34 | −29.22 | 106.16 | 102.01 | −4.15 |
| 229.68 | 180.63 | −49.05 | 200.04 | 208.06 | 8.02 |
| 262.8 | 218.55 | −44.25 | 247.39 | 236.37 | −11.02 |
| 311.5 | 231.33 | −85.17 | 316.03 | 301.11 | −14.92 |

Table I shows that the element without the polymer consistently underpredicted the ethanol concentration (Columns 2 and 3), while the element containing the polymer was much more accurate (Columns 5 and 6).

Example 2

This example illustrates an ethanol assay comparing an element of this invention containing polymer poly(acrylamide-co-2-acrylamido-2-methylpropane sulfonic acid, sodium salt) and an element without the polymer. The same keeping conditions and assay procedure were followed as described in Example 1. Results are shown in Table II.

can be effected within the spirit and scope of the invention.

We claim:

1. A multilayer analytical element for quantitatively assaying ethanol comprising a tetrazolium salt, alcohol dehydrogenase, NAD+, and an electron transfer agent wherein the layer comprising the electron transfer agent also includes a polymer having recurring negatively charged groups, and the alcohol dehydrogenase is in a different layer.

2. An element according to claim 1 wherein the polymer having recurring negatively charged groups is selected from the group consisting of poly(methyl acrylate-co-2-sulfo-1,1-di-methylethyl acrylamide-co-2-acetoacetoxyethyl methacrylate); poly(2-hydroxyethyl methacrylate-co-2-acrylamido-2-methylpropane sulfonic acid sodium salt-co-acetoacetoxyethyl methacrylate); poly(acryl-amide-co-2-sulfo-1,1-dimethylethyl acrylamide); and poly(acrylamide-co-2-acrylamido-2-methylpropane sulfonic acid, sodium salt).

3. The element according to claim 1 wherein the tetrazolium salt is selected from the group consisting of 3-(4,5-dimethyl(thiazolyl-2)2,5-diphenyl tetrazolium; 2-(4-iodophenyl)-3-(4-nitrophenyl)-5-diphenyl tetrazolium; 2,3,5-triphenyltetrazolium nitro blue tetrazolium; tetranitro blue tetrazolium; thiocarbamyl nitro blue tetrazolium and blue tetrazolium.

4. The element of claim 1, wherein the electron transfer agent is selected from the group consisting of 1-methoxy-5-methyl-phenazinium methyl sulfate, 5-methyl phenazine methosulfate, phenothiazine methosulfate and phenazine ethosulfate.

5. The element of claim 1 also comprising ascorbate oxidase in one of the layers.

6. The element of claim 5, wherein the ascorbate oxidase is in the same layer as the alcohol dehydrogenase.

TABLE II

| Keeping Comparison with AWna | | | | | |
|---|---|---|---|---|---|
| (Without Polymer) | | | (With Polymer) | | |
| Predicted Concentration Levels | Concentration After 3 Weeks Keeping (37° C.) (mg/dL) | Bias (mg/dL) | Predicted Concentration Levels (mg/dL) | Concentration After 4 Weeks Keeping (37° C.) (mg/dL) | Bias (mg/dL) |
| 1 | 2 | 3 | 4 | 5 | 6 |
| 0.01 | −4.46 | −4.46 | 0.00 | −4.46 | −4.46 |
| 81.27 | 78.78 | −2.49 | 83.86 | 87.56 | 3.7 |
| 104.09 | 95.98 | −8.11 | 106.96 | 111.65 | 4.69 |
| 106.93 | 99.57 | −6.66 | 108.75 | 109.72 | 0.97 |
| 229.55 | 207.35 | −22.2 | 233.94 | 239.08 | 5.14 |
| 237.64 | 211.51 | −26.1 | 254.42 | 252.7 | −1.72 |
| 316.15 | 273.35 | −42.8 | 316.2 | 305.8 | −10.47 |

Again, the element without the polymer consistently underpredicted the ethanol concentrations (Columns 2 and 3), while the test element containing the polymer was more accurate (Columns 5 and 6).

The invention has been described in detail with particular reference to preferred embodiments thereof, but it will be understood that variations and modifications 7. A multilayer element for the quantitative assay of ethanol in aqueous fluids, comprising a combination reagent/spreading layer and a reagent layer comprising a first and second zone, wherein the reagent/spreading layer comprises from 1 to 8 g/m² of a tetrazolium salt and from 2 to 8 g/m² of NAD+; the first reagent zone comprises from 5,000 to 20,000 U/m² of alcohol dehydrogenase; and the second reagent zone comprises from 0.01 to 0.2 g/m² of phenothiazine methosulfate and from 0.1 to 4 g/m² poly(methyl acrylate-co-2-sulfo-1,1-dimethylethyl acrylamide-co-2-acetoacetoxyethyl methacrylate).

8. The element of claim 7 wherein the first reagent zone comprises from 2000 to 12,000 U/m² of ascorbate oxidase.

* * * * *

UNITED STATES PATENT AND TRADEMARK OFFICE
CERTIFICATE OF CORRECTION

PATENT NO. : 5,294,540
DATED : March 15, 1994
INVENTOR(S) : Daniel S. Daniel, et. al.

It is certified that error appears in the above-indentified patent and that said Letters Patent is hereby corrected as shown below:

Col. 2, line 62, insert --Poly(acrylamide-co-2-sulfo-1,1-dimethylethyl acrylamide); and--

Col. 2, lines 57, 58, 59, 60, 62; and
Col. 4, lines 64, 65; and
Col. 6, lines 14, 16, 17, 18, 34; and
Col. 8, lines 2, 3, insert underline under each instance of "co".

Col. 4, line 68, insert underline under "supra".

Col. 6, line 40, insert ";" after 2,3,5-triphenyltetrazolium

Signed and Sealed this

Ninth Day of August, 1994

Attest:

BRUCE LEHMAN

Attesting Officer

Commissioner of Patents and Trademarks